United States Patent [19]

Fiorini et al.

[11] 4,413,142

[45] Nov. 1, 1983

[54] METHOD FOR PREPARING L-CARNITINE

[75] Inventors: Mario Fiorini; Claudio Valentini, both of Rome, Italy

[73] Assignee: Anic S.p.A., Palermo, Italy

[21] Appl. No.: 358,326

[22] Filed: Mar. 15, 1982

[30] Foreign Application Priority Data

Mar. 18, 1981 [IT] Italy ............................... 20396 A/81

[51] Int. Cl.$^3$ ........................................... C07C 101/30
[52] U.S. Cl. .................................. 562/567; 549/450; 549/453; 549/455; 568/844; 260/456 P; 260/465.5 R; 260/465.6
[58] Field of Search ......................................... 562/567

[56] References Cited

U.S. PATENT DOCUMENTS 3,151,149  9/1964  Strack ................................. 562/567
4,296,242  10/1981  Nagabhushan ..................... 562/567

FOREIGN PATENT DOCUMENTS 1281230  12/1961  France .............................. 562/567

*Primary Examiner*—Michael L. Shippen
*Attorney, Agent, or Firm*—Hedman, Casella, Gibson, Costigan & Hoare

[57] ABSTRACT

L-carnitine is prepared by a synthesizing process starting from D-mannitol. The synthesis is started with the formation of a D-mannitol ketonide (more specifically D-mannitol acetonide from D-mannitol and acetone, whereafter the D-mannitol is split by oxidation to give glyceraldehyde acetonide, which is further reduced to glycerol acetonide. Then the free hydroxyl group is exchanged with a halogen atom (chlorine) with the formation of chlorodihydroxy propane, the primary alcoholic group of which is functionalized with the acid chloride of a sulfonic acid (tosylchloride). The reaction of the tosyl derivative with the salt of hydrogen cyanide leads to the formation of the corresponding nitrile which, when reacted with trimethylamine gives carnitinonitrile. The nitrile group is now hydrolyzed to give L-carnitine chloride. The formation of L-carnitine can then be obtained by exchanging the chloride ion with a hydroxyl ion.

44 Claims, No Drawings

METHOD FOR PREPARING L-CARNITINE

This invention relates to a process for the chemical synthesis of L-carnitine starting from D-mannitol.

L-carnitine is a gamma-hydroxy aminoacid having the following formula:

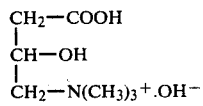

This compound, which is also known as the Vitamine $B_T$, is conventionally known as a hydroxyaminoacid which promotes the mitochondrial oxidation of the fatty acids, to produce energy at the level of the muscular system.

Its most commonly known therapeutic use is as an eutrophic agent, although it has been recently suggested to use it in four new therapeutic fields, viz.: chronic haemodyalisis, correction of the atherogenic lipoproteinic pattern, suppression of heart arrythmia, during infaractual seizures and the therapy by infusion.

It is known that L-carnitine is obtained by synthetic chemical processes which starts all from products which are not optically active, or from mixtures of racemates. The most commonly used among these products are epichlorohydrin and ethyl acetoacetate. At any rate, the obtention of the individual optical antipodes of L-carnitine from the racemate mixture is effected at the level of the last steps of the synthesis with the known procedure of the fractional crystallization by means of optically active acids.

More precisely, by using D-camphoric acid on the racemate mixture of DL-carnitinamide it is possible to prepare, by hydrolysis with HCl, the L-carnitine chloride.

Another method is that of the resolution of the racemic mixture of the two isomers of carnitinonitrile by sequentially using camphoric acid and dibenzoyl tartaric acid, both optically active.

It is fully apparent that the process according to the present invention affords, as compared with the old synthesizing methods, the advantage of being economically more acceptable because, with the old fractional crystallization methods the maximum yield is only 50% for each individual stage and 50% of the product which could be obtained is thus lost, that which does not occur if an optically pure starting product is used.

The process according to the present invention permits to obtain the acid chloride of L-carnitine starting from an optically active compound such as D-mannitol.

Said process is carried out according to the following step sequence:

(a) reaction of D-mannitol with a ketone so as to obtain the diketonide derivative.
(b) oxidative splitting of said derivative to obtain the (R) glyceraldehyde ketonide.
(c) reduction of the glyceraldehyde ketonide to glycerol- (S)-1,2-ketonide.
(d) replacement of the free alcoholic group of the glycerol- (S)-1,2-ketonide by a halogen atom so as to obtain the relative halogen-derivative.
(e) hydrolysis in an acidic environment of the halogenated derivative to obtain the (R)-1,2-dihydroxy-3-halogen-propane.
(f) functionalisation of the primary alcoholic group of the (R)-1,2-dihydroxy-3-halogen-propane with a sulphonic acid to obtain the corresponding ester.
(g) reaction between said ester and a salt of hydrogen cyanide to give the corresponding nitrile.
(h) reaction between the nitrile aforementioned and th trimethylamine to give the carnitinonitrile and
(i) hydrolysis of the nitrile group to a carboxyl group to obtain the L-carnitine acid halide.

More detailedly, the processing stages listed above are carried out under the following working conditions and using the particular reagents to be specified hereinafter, which, however, are not to be construed as limitations but as preferred and not exclusive embodiments of the invention.

(a) In the preparation of the diketonide deriving from D-mannitol acetone is the ketone which is preferentially used. Then, the 1,2,5,6-diacetone D-mannitol is prepared by reacting acetone, to which solid zinc chloride has been added, with D-mannitol with stirring within a temperature range of from 0° C. to +50° C.

(b) The oxidative splitting of 1,2,5,6-diacetone-D-mannitol can indifferently be carried out in either of the following two ways:
  (1) by reacting the D-mannitol diacetonide dissolved in an appropriate solvent, such as tetahydrofuran, with lead acetate Pb(CH$_3$COO)$_4$ within a temperature range of from −20° C. to +20° C., and in a molar ratio of 1:1.
  (2) by reacting the D-mannitol diacetonide with Pb$_3$O$_4$ and acetic acid, possibly in a solvent medium such as chloroform, at a temperature comprised between −20° C. and +20° C. and with a slight defect of weight (about 10% by wt) of D-mannitol.

(c) The reduction of the (R) glyceraldehyde acetonide to (S)-glycerol-1,2-acetonide is carried out with a reducing agent such as sodium borohydride NaBH$_4$ in an alkaline environment and with stirring, while maintaining the temperature within the range of from +30° C. to +10° C. The molar ratio of sodium borohydride to (R) glyceraldehyde is roughly 2.

(d) The alcoholic group as obtained by the reaction of the aldehyde group must be substituted by a halogen, chlorine being preferred.

Thus, there is obtained the (R)-2,2-dimethyl-4-chloromethyl-1,3-dioxolan, which is prepared by reacting the (S) glycerol-1,2-diacetonide, dissolved in an appropriate solvent, such as benzene, with a stoichiometrical amount of triphenylphosphine (1.05:1) and an excess of carbon tetrachloride (3:1 or 4:1) an amine base being present, such as 2,6-lutidine, in an amount of from 2% to 10% (molar), and refluxing the reaction mixture during one hour (temp. 80° C.–100° C.). Other sterically hindered amines can be also used, such as triisopentylamine or ethyl-diisopropylamine. In such a case, the CCl$_4$, in addition to unfonding its action as a chlorinating agent, has also the function of a solvent. If so desired, the reaction can also be conducted without benzene or another solvent being present, because one exploits the solvent power of carbon tetrachloride as such. As an alternative, the product can be prepared by working at a temperature comprised between +10° C. and +100° C. in piridine during 3 hours or longer, using a stoichiometrical amount of CCl$_4$ and an amount of triphenylphosphine P(C₆H₅)₃ which is twice the molar amount of glycerol acetonide (molar ratio 2:1).

The (R)-3-chloro-1,2-propanediol is obtained from the (R)-2,2-dimethyl-4-chloromethyl-1,3-dioxolan by acidic hydrolysis with diluted HCl in a medium which is composed of p-dioxan, or with aqueous acetic acid within a temperature range comprised between +20° C. and +100° C.

(f) The functionalization of the primary alcoholic group of the 1,2-dihydroxy-3-chloro propane is carried out by means of tosyl chloride

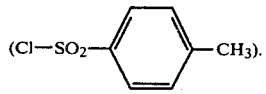

or by means of mesyl chloride (ClSO₂CH₃) or by naphthyl sulphochloride

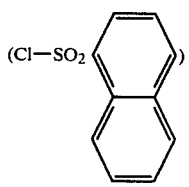

or sulphonyl chloride of the kind, by reaction with dihydroxychloropropane in piridine, alone or in a mixture with other solvents such as tetrahydrofuran, chloroform, ethers, at a temperature comprised between −20° C. and +30° C. Tosyl chloride is used in excess up to 10% molar relative to the substrate to be functionalized.

(g) The nitrilation of the tosyl derivative indicated above is obtained by reaction with an alkali metal cyanide such as KCN also in a slight excess relative to the stoichiometrical amount in a temperature range comprised between 0° C. and +50° C. and in solvents such as methanol, ethanol, water, dimethylsulphoxide and dimethylformamide.

(h) The carnitinonitrile is prepared by reacting (R)-2-hydroxy-3-chlorobutyronitrile with trimethylamine (in excess), in a solvent medium consisting of water, or ethanol, or dioxan, or like solvent, at a temperature comprised between +40° C. and +100° C. Trimethylamine can be used, either in aqueous solution or anhydrous.

(i) The hydrolysis of the nitrile group of the carnitinonitrile with concentrated hydrochloric acid (concentration 37%, about 11 times that of the normal solution, or with gaseous hydrogen chloride HCl but using ethanol as the solvent, is carried out within the temperature range comprised between +30° C. and the refluxing temperature of the solvents. Said reaction is conducive to the formation of L-carnitine acid chloride.

The end product can be converted into L-carnitine by exchanging the chloride ion by the hydroxyl ion. This reaction can be carried out according to the procedures which are known to anyone skilled in the art, such as for example the flow of the solution of L-carnitine acid chloride on an ion exchange resin of the hydroxyl form, or by treating said acid chloride with a solution of a strong base, such as ammonium hydroxide, and the removal of ammonium chloride.

The process according to this invention can be diagrammatically represented as follows:

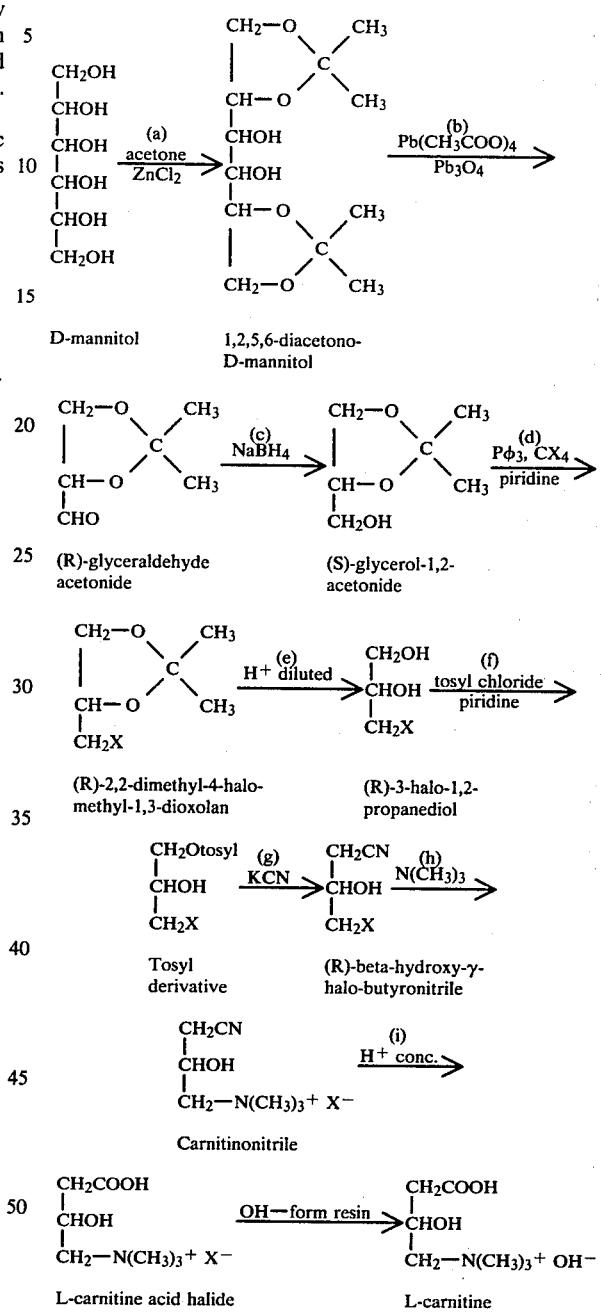

The following examples are preferred embodiments of the invention and do not limit its scope.

STEP (A)

Preparation of the 1,2,5,6-diacetone-D-mannitol 270 grams of ZnCl₂, in solid form, have been added to 1350 mls of acetone, in a 2-liter flask. The closed flask is stirred slowly to assist the dissolution of the zinc chloride, that which takes place with a considerable heat build up: the operation is continued until only a slight portion of solid residue is left in the flask. The acetone solution of zinc chloride is allowed to cool at room temperature and allowed to stand so as to settle the major fraction of insoluble matters. In a 3-liter flask equipped with a mechanical stirrer capable of operating under anhydrous conditions, there are charged 170 grams of D-mannitol (finely powdered) preferably with a grit size of 200 mesh), whereafter there is added thereto, by decantation, the slightly turbid solution of zinc chloride in acetone, while trying to avoid, as far as practicable, the transfer of the portion which is left dissolved in water. The mixture is vigorously stirred so as to dissolve the maximum possible fraction of mannitol and this operation takes two hours and is carried out at a temperature of about 20° C. The solution is then filtered so as to remove the unreacted mannitol (about 40 grams) and the filtrate is treated immediately after in the following manner.

In a 5-liter flask having an efficient stirring mechanism a solution is prepared, which is composed of 340 grams of anh. potassium carbonate and 340 mls of water. Upon cooling of the solution at room temperature, the liquor is blanketed by a layer of 1350 mls of pure ether which must be completely devoid of ethanol. The mixture is vigorously stirred while concurrently adding thereto as quickly as practicable the solution in acetone which has been filtered beforehand. Stirring is continued during a time of 30 to 40 minutes, whereafter the solution is ether and acetone is decanted and the zinc carbonate lumps are washed with discrete portions (totalling 300–400 mls) of a mixture of acetone and ether in a 1:1 ratio. The combined solutions are dried with stirring, by adding 340 grams of anh. potassium carbonate thereto during 30 minutes. The solution is filtered and the carbonate is washed with several portions of a 1:1 mixture consisting of acetone and ether (totalling 300–400 mls).

The filtrates and the washing liquors, combined, are evaporated under reduced pressures and the residue is thoroughly vacuum-dried at 60° C.–70° C. (water bath) during 2 hours. The distillation flask is transferred onto an oil bath, there are added 400 mls of nor.butyl ether, whereafter the temperature of the bath is raised to 135° C. The hot solution is quickly filtered through a water-heated funnel and 75 mls of hot butyl ether are added at the end of the operation to wash both the flask and the filter. The filtrate, which solidifies immediately, is maintained at a low temperature during several hours.

The precipitate is vacuum-filtered, washed on the filter with a low-boiling petroleum ether and vacuum-dried. The yield of 1,2,5,6-diacetone-D-mannitol (m.p. 117° C.–119° C.) which is pure enough, is 90 g–103 g (50%–55% of theory, based on the quantity of mannitol dissolved in the reaction mixture). The recrystallization of this substance in a quantity of hot butyl ether six times its weight, raises its melting point to 120° C. The recrystallization from water, in which the acetone derivative is very soluble, makes it possible to obtain a very pure substance (m.p. 122° C.), altough at the expense of a slight weight drop. This notwithstanding, the compound having such a melting point (119° C.) is pure enough to be utilized afterwards.

STEPS (B) AND (C)

Preparation of (S)-glycerol-1,2-glycerol-1,2-acetonide, preceded by the synthesis of the (R)-aldehyde-1,2-acetonide (1) A chilled solution of 1,2,5,6-diacetone-D-mannitol (80.0 g=0.3 mol) in THF (tetrahydrofuran) (400 mls) is incrementally supplemented, with stirring, with 134 g (0.3 mol) of dry Pb(O Ac)$_4$, the temperature being maintained below 10° C. The solution is stirred for 30 minutes on an ice bath and for 30 additional minutes out of the bath. Upon filtration and another introduction into an ice bath, a solution of NaBH$_4$ (22.9 g=0.61 mol) in 4% aqueous sodium hydroxide (400 mls) is dripped thereinto with vigorous stirring, the temperature being maintained below 10° C.

After stirring the solution on an ice bath for 30 minutes and at room temperature for 90 minutes thereafter, the solution is supplemented with solid ammonium chloride to adjust the pH to 8. Tetrahydrofuran is distilled off under reduced pressures and the aqueous solution thus obtained is saturated with sodium chloride. Upon extraction with ethyl acetate, the organic phase is washed with 5% aqueous NaOH, saturated with sodium chloride which has previously been dried over Na$_2$SO$_4$ and concentrated. By distillation, one obtains pure glycerol-1,2-acetonide. (58,4 g; yield 73%), m.p. 80° C.–90° C. (20 mmHg) $^1$H NMR (CdCl$_3$, 1,35 (3H, s), 1,45 (3H,s), 3,5–4,5 (6H,m).

$D^{25}$ 11.3° (c 5,175, CH$_3$OH).

(2) (S')-glycerol-1,2-acetonide can also be obtained by adopting the following alternative procedure.

20 grams of D-mannitol acetonide (76.5 millimol) are dissolved in 300 mls of distilled CHCl$_3$ and supplemented by 52.6 g of Pb$_3$O$_4$ (76.7 mols). To the latter solution there are added 37.76 g of distilled glacial acetic acid (628.8 millimol) diluted in 100 mls of CHCl$_3$, this addition being completed within 2 hours.

The entire mixture is maintained vigorously stirred mechanically and, after 2 hours, it tends to lump up whereas the temperature tends to rise (T=22° C. from a starting 20° C.), the temperature is brought back to 20° C. and a slow decoloration is observed (from the starting brick-red). After a 66-hour stirring, the solution is white but the GLC (gas-liquid chromatography) indicates the presence of unreacted mannitol diacetonide, so that a supplement of the 10% of the initial amount of Pb$_3$O$_4$ is added (5.3 g) together with the 10% of the starting CH$_3$COOH (3.6 mls) diluted in 10 mls of CHCl$_3$, to improve the conversion. The reaction mass is now rosy and is filtered after stirring for 4½ additional hours (under nitrogen blanket). A rosy solid is separated together with a solution that at GLC shows a conversion into aldehyde which equals 98% of the unreacted mannitol diacetonide.

The solid phase is washed with CHCl$_3$ to remove any residual traces of aldehyde. Thereafter, a saturated solution of NAHCO$_3$ is added to neutralize the excess CH$_3$COOH (pH 8.5). CHCl$_3$ is reduced by using 5.9 g of NaBH$_4$ in 100 mls of 4%-NaOH. From the GLC analysis it has been ascertained that the conversion into alcohol is as high as 99% of the unreacted mannitol diacetonide. The pH of the solution obtained from the reduction is adjusted from 11.2 to 9.2 with NH$_4$Cl. With a separatory funnel, the aqueous phase is separated from the chloroform phase and the aqueous phase is subsequently extracted with small volumes of CHCl$_3$ to recover the alcohol which has been left therein. The entire chloroform phase is dried over Na$_2$SO$_4$ and concentrated in a rotary evaporator to remove CHCl$_3$. The alcohol is then distilled under reduced pressures (mechanical pump) and the GLC analysis of the distillate gives the pure alcoholic phase, a few traces only of CHCl$_3$ being excepted. The yield of alcohol is 73.7%.

The optical rotatory power of the alcohol has been measured by weighing 500 milligrams of the alcohol and making them up to a volume of 10 mls with CH₃OH. A value of $[\alpha]_D^{20}$ of 11.64° has been obtained, whereas the value of $[\alpha]_D^{20}$ as reported in the literature is 11.3°.

STEP (D)

Preparation of the 2,2-dimethyl-4-(R)-chloromethyl-1,3-dioxolan 1. 13.2 g (0.10 mol) of glycerol-1,2-acetonide are dissolved into 50 mls benzene with 27.5 g (0.105 mol) of Pφ₃ (triphenylphosphine) and 0.4 ml of 2,6-lutidine and the mixture is added dropwise during 30 minutes to CCl₄ maintained under reflux and containing an additional amount of the base (0.2 ml). After 30 minutes, the reaction mixture is subjected to fractionation, thus obtaining 13.5 g of a product (yield 89%) having a m.p. of 51° C. (12 mmHg) $[\alpha]_D^{20}$ (pure liquid) = +46.2°; $d_4^{20} = 1.1054$; ($M_4^{20} = 62°$).

2. The same product can be obtained according to the following procedural conditions:

A 500-ml flask is charged with 106 g of Pφ₃ (MW 262) with 150 mls piridine and 26.7 g of the acetonide (½ molar relative to Pφ₃). Then, there are introduced 20 mls of CCl₄ (molar relative to the acetonide) in 25 mls piridine dropwise, with cooling. The reaction mixture is maintained at room temperature during 3 hours and then to 40° C. for 30 minutes. The mixture is filtered and the filtrate is washed with Et₂O. There are now added 125 mls of MeOH to destroy the excess reactant and 250 mls of Et₂O in total.

Thereafter, conc. HCL is added until two phases are formed. The ethereal phase is put aside and the aqueous piridine-containing phase is extracted with a total of 600 mls of Et₂O. Subsequently, the ethereal phase is washed with 1-normal HCl until an acidic reaction is found for water, to remove piridine. The mixture is dried over Na₂SO₄ and concentrated in a rotary evaporator and the solid is collected on a filter, whereafter a fraction of 21 g of (R)-2,2-dimethyl-4-chloromethyl-1,3-dioxolan is distilled, which shows a $[\alpha]_D^{20}$ of +46.430°.

STEP (E)

Preparation of the 3-Cl-1,2-propanediol (R)

1. 15.05 g (0.1 mol) of 2,2-dimethyl-(R)-4-ClCH₂-1,3-dioxolan are refluxed for two hours in 100 mls of ½-normal aqueous HCl, to which 100 mls of p-dioxan had previously been added.

Upon homogeneization of such a heterogeneous mixture, the whole is evaporated (12 mmHg) and the residue is thrice extracted with 100 mls of CHCl₃. The organic phase is evaporated and the residue virtually consists of pure (R)-3-Cl-1,2-propanediol. The yield is 11 g $[\alpha]_D^{22} = 1.3°$.

2. The same product can also be obtained by the following procedure. A mixture composed of 49.5 g of 2,2-dimethyl-4-chloromethyl-1,3-dioxolan and 350 mls of 10% aqueous acetic acid is heated with vigorous stirring to 60° C. for two hours. On evaporation of the resultant clear solution under reduced pressures, the residue is supplemented with 50 mls water, which are then removed again by evaporation so as to remove the last traces of acetic acid. The product is then dried by adding 100 mls benzen thereto and is subsequently evaporated. The residue is purified by distillation and there are obtained 33.9 g (93%) of 3-chloro-1,2-propanediol, having, under a pressure of 19 mmHg a b.p. of 122.5° C.-124° C., the $[\alpha]_D^{22}$ being −1.32°.

STEP (F)

Preparation of the (R)-3-chloro-2-hydroxy-1-o.tosyl-propanol

To 2 g of (R)-3-chloro-1,2-propanediol (18.1 millimols) in 20 mls of piridine there are added at 0° C. in very small increments and while maintaining the temperature to 0° C., 4.00 g of tosyl chloride (20 millimols). On completion of such addition, the mixture is allowed to react for 1 hour at room temperature, whereafter it is treated with 2-normal HCl in ice. The mixture is extracted with CHCl₃ (3 times 100 mls), whereafter the mixture is dried over anh.Na₂SO₄, is filtered and treated in a rotovapor. On completion of this stage, there are obtained 3.6 g of (R)-3-chloro-2-hydroxy-1-o.tosyl propanol, which corresponds to a yield of 75%.

The compound has been identified in NMR as follows:

| | |
|---|---|
| CH₂Cl | 2.40 (3H.CH₃); 3.30–4.40(5H—CH₂Cl, CH₂O, CHOH); |
| CHOH | 2.80 (broad, 1H, OH); 7.20–8.0(4H.φ). |
| CH₂O—tosyl | solvent: deuterated CHCl₃. |

STEP (G)

Preparation of the (R)-3-chloro-2-hydroxy-butyronitrile

To a mixture containing 19.35 g of (R)-3-chloro-2-hydroxy-1-tosyl propanol (73.1 millimols) and 7.65 g (18 millimols) of (R)-1-chloro-2,3-ditosyl propane dissolved in 120 mls of MeOH, there are added 5.94 g of KCN (91 millimols) and the reaction is allowed to proceed at room temperature during 40 hours. The potassium tosylate is removed by filtration and the product is distilled with a rotary pump at 80° C., whereby 5 g of a compound are obtained, which, upon analysis, has proven to be (R)-3-chloro-2-hydroxy butyronitrile. Thus, a yield of 60% is obtained. The compound has been identified by NMR (the solvent was deuterated methanol).

| | |
|---|---|
| CH₂Cl | 2.80 (d 2H, CH₂CN), 3.65 (d 2H, CH₂Cl) |
| CHOH | 4.22 (m, 1H, CHOH) |
| CH₂CN | |

STEP (H)

Preparation of the (R)-carnitinonitrile

To 5.1 g of (R)-3-chloro-2-hydroxy butyronitrile there are added 15.3 g of a 33% aqueous solution of trimethylamine. The mixture is slowly refluxed (about 90° C.) and is allowed to reflux for 45 minutes. Water and (CH₃)₃N are withdrawn and crystallization from 96%-EtOH is carried out to obtain 4.5 g (yield 60%) of (R)-carnitinonitrile.

$[\alpha]_D^{22} = 26.07°$ (c=1.99 H₂O); The compound has been identified at NMR analysis as follows:

| | | |
|---|---|---|
| CH$_2$N+ | (CH$_3$)$_3$Cl⁻ | 3.0 (d 2H, CH$_2$CN) 3.41 (9H, N(CH$_3$)$_3$) |
| CHOH | | 3.65 (d 2H, CH$_2$N) 4.80 (m, 1H, CHOH) |
| CH$_2$CN | | solvent deuterium oxide. |

STEP (I)

Preparation of the (R)-carnitine acid chloride 3.5 g of (R)-carnitinonitrile are dissolved in 6 g of conc. (37%) HCl and refluxed for 4 hours. The reaction mixture is allowed to cool and water, HCl and NH$_4$Cl are withdrawn by the pump. The residue is taken up with 50 mls of acetonitrile and ether is added until the liquid is turbid. The carnitine acid chloride requires many hours to crystallize. The yield is 83%.

We claim:

1. A process for the preparation of L-carnitine starting from D-mannitol comprising the steps of reacting D-mannitol with a ketone, subjecting the thusly obtained D-mannitol diketonide to an oxidative splitting reaction to obtain a glyceraldehyde ketonide, treating the latter compound with a reducing agent of the aldehyde class, substituting the alcoholic group of the glycerol acetonide thus obtained by a halogen atom, subjecting the halogenated derivative to acidic hydrolysis to obtain the halogenated dihydoxypropane, esterifying the primary alcoholic group of the latter compound with the acid chloride of a sulphonic acid, reacting said ester with a salt of hydrogen cyanide to obtain the corresponding nitrile, treating said nitrile with trimethylamine so as to obtain the carnitinonitrile, subjecting the nitrile group thereof to acidic hydrolysis to build up the corresponding carboxyl group, effecting an ion-exchange between the halide ion of the L-carnitine acid halide and a hydroxyl ion and separating the thusly obtained L-carnitine.

2. A process for the preparation of L-carnitine according to claim 1, characterized in that in the reaction of D-mannitol with a ketone, the ketone is acetone.

3. A process for the preparation of L-carnitine according to claim 2, characterized in that the reaction of the D-mannitol with acetone is carried out with zinc chloride being present.

4. A process for the preparation of L-carnitine according to claim 3, characterized in that the reaction of D-mannitol with acetone is carried out within a temperature range between 0° C. and +50° C.

5. A process for the preparation of L-carnitine according to claim 1, characterized in that the oxidative splitting of the D-mannitol diacetonide is carried out by reacting the latter with Pb$_3$O$_4$ and acetic acid.

6. A process for the preparation of L-carnitine according to claim 5, characterized in that the lead tetroxide and the D-mannitol diacetonide are caused to react in a molar ratio comprised between 1.1 and 1.3, the value of 1.2 being preferred.

7. A process for the preparation of L-carnitine according to claim 6, characterized in that said oxidative splitting of the D-mannitol diacetonide is carried out within a solvent medium.

8. A process for the preparation of L-carnitine according to claim 7, characterized in that the solvent is chloroform.

9. A process for the preparation of L-carnitine according to claim 8, characterized in that the oxidative splitting of the D-mannitol diacetonide is carried out within a temperature range of between −20° C. and +20° C.

10. A process for the preparation of L-carnitine according to claim 1, characterized in that the reducing agent for the glyceraldehyde acetonide is sodium borohydride NaBH$_4$.

11. A process for the preparation of L-carnitine according to claim 10, characterized in that the glyceraldehyde acetonide is put to react with sodium borohydride in a molar ratio NaBH$_4$-to-glyceraldehyde acetonide comprised between 1.8 and 2.2.

12. A process for the preparation of L-carnitine according to claim 11, characterized in that the reaction between glyceraldehyde acetonide and sodium borohydride is carried out at a pH value higher than 7.

13. A process for the preparation of L-carnitine according to claim 12, characterized in that the reaction between glyceraldehyde acetonide and sodium borohydride is carried out within a temperature range of between −10° C. and +30° C.

14. A process for the preparation of L-carnitine according to claim 1, characterized in that the halogen which substitutes the alcoholic group of the glycerol acetonide is chlorine.

15. A process for the preparation of L-carnitine according to claim 14, characterized in that the replacement of the alcoholic group of the glycerol acetonide by a chlorine atom leads to the formation of (R)-2,2-dimethyl-4-chloromethyl-1,3-dioxolan.

16. A process for the preparation of L-carnitine according to claim 15, characterized in that the preparation of (R)-2,2-dimethyl-4-chloromethyl-1,3-dioxolan is carried out by reacting glycerol acetonide with carbon tetrachloride and triphenyl phosphine, an amine base being present.

17. A process for the preparation of L-carnitine according to claim 16, characterized in that the amine base is piridine.

18. A process for the preparation of L-carnitine according to claim 17, characterized in that in the reaction for replacing the alcoholic group of the glycerol acetonide, carbon tetrachloride, triphenyl phosphine and piridine are reacted in a molar ratio, relative to the glycerol acetonide, of 1,2 and 3:10, respectively.

19. A process for the preparation of L-carnitine according to claim 14, characterized in that the reaction for replacing the alcoholic group by chlorine is carried out within a temperature range of from +10° C. and +100° C.

20. A process for the preparation of L-carnitine according to claim 15, characterized in that the acidic hydrolysis of the (R)-2,2-dimethyl-4-chloromethyl-1,3-dioxolan is carried out by reacting the latter compound with a diluted acid.

21. A process for the preparation of L-carnitine according to claim 20, characterized in that the diluted acid is a member selected from the group consisting of hydrochloric acid and acetic acid.

22. A process for the preparation of L-carnitine according to claim 21, characterized in that if the diluted acid is hydrochloric acid, the reaction is carried out within a solvent medium.

23. A process for the preparation of L-carnitine according to claim 22, characterized in that the solvent medium is p-dioxan.

24. A process for the preparation of L-carnitine according to claim 20 and 23, characterized in that the acidic hydrolysis of the (R)-2,2-dimethyl-4-chloromethyl-1,3-dioxolan is carried out within a temperature range of from +20° C. and +100° C.

25. A process for the preparation of L-carnitine according to claim 14, characterized in that the esterification of the primary alcoholic group of the chlorodihydroxypropane is carried out by reacting the latter compound with the acid chloride of a sulphonic acid in a solvent medium.

26. A process for the preparation of L-carnitine according to claim 1, characterized in that the acid chloride of a sulphonic acid is a member selected from the group consisting of tosyl chloride, mesyl chloride and naphthyl sulphochloride.

27. A process for the preparation of L-carnitine according to claim 26, characterized in that the acid chloride of a sulphonic acid is preferably tosyl chloride.

28. A process for the preparation of L-carnitine according to claim 27, characterized in that the reaction of esterification of the primary alcoholic group of the chlorodihydroxypropane is carried out by employing tosyl chloride and chlorodihydroxypropane in a molar ratio comprised between 1.05 and 1.2.

29. A process for the preparation of L-carnitine according to claim 25, characterized in that the reaction of esterification of the primary alcoholic group of the chlorodihydroxypropane is carried out within a solvent medium consisting of piridine.

30. A process for the preparation of L-carnitine according to claim 1, characterized in that the reaction of esterification of the primary alcoholic group of the chlorodihydroxypropane is carried out in a solvent medium consisting of piridine admixed with another solvent which is a member selected from the group consisting of the ethers, tetrahydrofuran and chloroform.

31. A process for the preparation of L-carnitine according to claim 1, characterized in that the reaction of esterification of the primary alcoholic group of the chlorodihydroxypropane is carried out within a temperature of from −20° C. to +30° C.

32. A process for the preparation of L-carnitine according to claim 1, characterized in that the ester of the chlorodihydroxypropane with the sulphonic acid is reacted with a salt of hydrogen cyanide with an alkali metal within a solvent medium.

33. A process for the preparation of L-carnitine according to claim 32, characterized in that the nitrile which has been formed is the (R)-2-hydroxy-3-chlorobutyronitrile.

34. A process for the preparation of L-carnitine according to claim 32, characterized in that the salt of hydrogen cyanide with an alkali metal is preferably potassium cyanide.

35. A process for the preparation of L-carnitine according to claims 1, 32 and 34, characterized in that the molar ratio of potassium cyanide to the chlorodihydroxypropane ester is comprised between 1.01 and 1.1.

36. A process for the preparation of L-carnitine according to claim 32, characterized in that the solvent medium is a member selected from the group consisting of methanol, ethanol, water and dimethylsulphoxide.

37. A process for the preparation of L-carnitine according to claim 32, characterized in that the ester of chlorodihydroxypropane with the sulphonic acid is reacted with a salt of hydrogen cyanide within a temperature range between +10° C. and +50° C.

38. A process for the preparation of L-carnitine according to claim 1, characterized in that the carnitinonitrile is obtained by reacting (R)-2-hydroxy-3-chlorobutyronitrile with trimethylamine.

39. A process for the preparation of L-carnitine according to claim 38, characterized in that the reaction is carried out within a solvent medium which is a member selected from the group consisting of water, ethanol and dioxan.

40. A process for the preparation of L-carnitine according to claim 38, characterized in that the reaction is carried out within a temperature range between +40° C. and +100° C.

41. A process for the preparation of L-carnitine according to claim 1, characterized in that the carnitinonitrile is subjected to acidic hydrolysis to produce L-carnitine acid chloride.

42. A process for the preparation of L-carnitine according to claim 1, characterized in that the acidic hydrolysis is carried out with hydrochloride acid.

43. A process for the preparation of L-carnitine according to claim 42, characterized in that the reaction is carried out within a polar solvent medium, ethanol being preferred.

44. A process for the preparation of L-carnitine according to claim 42, characterized in that the reaction is carried out within a temperature range between +30° C. and the reflux temperature of the solvent.

* * * * *